United States Patent [19]

Hafele et al.

[11] Patent Number: 4,685,066
[45] Date of Patent: Aug. 4, 1987

[54] CONTAMINATION MONITOR AND METHOD

[75] Inventors: Joseph C. Hafele, Peoria; John W. Crayton, Washington, both of Ill.

[73] Assignee: Caterpillar Inc., Peoria, Ill.

[21] Appl. No.: 683,106

[22] Filed: Dec. 18, 1984

[51] Int. Cl.⁴ .................................... G01N 11/04
[52] U.S. Cl. ................... 364/509; 364/510; 364/572; 210/90; 73/54; 73/55
[58] Field of Search ............... 364/509, 510, 550, 551, 364/558, 572; 210/90, 87, 85; 116/220, 70; 73/3, 4 R, 54, 55, 56

[56] References Cited

U.S. PATENT DOCUMENTS

| | | | |
|---|---|---|---|
| 3,033,030 | 5/1962 | Heller | 73/118 |
| 3,357,236 | 12/1967 | Kasten | 73/61 |
| 3,499,315 | 3/1970 | Marino | 73/61 |
| 3,610,026 | 10/1971 | Tophan | 73/55 |
| 3,678,881 | 7/1972 | Shinn | 116/70 |
| 3,878,461 | 4/1975 | Saint-Andre | 324/61 |
| 3,924,448 | 12/1975 | Howard et al. | 73/55 |
| 4,038,189 | 7/1977 | Dison et al. | 210/90 |
| 4,246,110 | 1/1981 | Jarrett | 210/90 |
| 4,271,402 | 6/1981 | Kastura et al. | 340/52 |
| 4,332,679 | 6/1982 | Hengst et al. | 210/90 |
| 4,348,653 | 9/1982 | Tsuzuki et al. | 340/52 |
| 4,384,472 | 5/1983 | Tournier | 73/55 |
| 4,386,518 | 6/1983 | Zatko | 73/55 |
| 4,442,704 | 4/1983 | Swearingen | 73/55 |
| 4,581,707 | 4/1986 | Millar | 364/509 |

OTHER PUBLICATIONS

Dammer, "Fixed Resistors", 1956, p. 34, *Radio and Electronic Components*, vol. 1.
Murphy, "Basic Automatic Control Theory", 1967, pp. 18-19.
Lindeburg, "Engineer in Training Review Manual", Sixth Edition, 1982, pp. 16-10, 16-11.
Literature on "The Oil Monitor" introduced by Carr-Tech Distributing Limited at the World Truck Symposium in Detroit, USA in late 1981.

*Primary Examiner*—Gary Chin
*Assistant Examiner*—Thomas G. Black
*Attorney, Agent, or Firm*—Charles E. Lanchantin, Jr.

[57] ABSTRACT

A contamination monitor for sensing particle contamination in a liquid system having a filter includes a sensor for measuring the pressure differential across the filter, a reference apparatus for providing information relative to at least one of the viscosity changes and the flow changes of the liquid passing through the filter by providing one or more reference signals relating thereto, and a programmable data processing and interface unit for receiving data from the sensor and the reference apparatus and providing a recognizable compensated output corresponding to the contamination level of the liquid system. The data processing and interface unit can provide a plurality of command signals for lighting a plurality of lights that can be individually used for diagnostic purposes and can provide information on the rate of plugging of the filter.

17 Claims, 6 Drawing Figures

CONTAMINATION MONITOR AND METHOD

TECHNICAL FIELD

This invention relates generally to a monitor for quantifying the amount of particle contamination in a liquid system, and more particularly to a contamination monitor and method for continuously sensing the condition of a system filter and any abnormal degree of increase in the ingress of particulate contamination.

BACKGROUND ART

There are a considerable number of indicators available which actively measure the pressure drop across a filter. When the pressure drop gets high enough a suitable indicating reference signal is provided and the operator knows it is time to replace the filter. These indicators are not too reliable because they do not provide any compensation for variations in the viscosity of the liquid or the flow through the filter. It can be appreciated that such indicators are not very satisfactory for vehicular implement, transmission or engine systems because the viscosity of the oils and liquids used therein significantly increases at cold temperatures and the flow through the filter varies across a relatively wide range.

Recommended filter change periods are usually published or posted, but there is still no inexpensive way to know between these theoretical intervals if the filter element is plugged, if the filter is ruptured, or if the contamination rate is excessively high. Usually, an operator does not notice a problem until serious damage has already occurred in the liquid system.

Several electro-optical systems are known for directing a light beam through the liquid and providing from scattered light a signal proportional to the particle concentration. But these systems are expensive, are not as reliable as desired since air bubbles can affect results, and do not give a reading on the condition of the filter.

Other systems operate on a magnetic principle so that the degree of contamination by non-metallic particles is not measured.

U.S. Pat. No. 3,499,315 issued Mar. 10, 1970 to J. A. Marino discloses another method of determining contamination in a fluid system by recording the pressure differential produced across a filter element. However, it involves temporary connections and undesirable controlling of the flow so that it is not an integrated system with diagnostic capability, but rather is more of a specialized test set up.

Accordingly, what is needed is an improved contamination monitor for detecting and quantifying the amount of liquid-borne contamination in a vehicle liquid system or the like, and for operationally communicating with the system service filter and indicating the condition thereof while compensating for viscosity and flow. Preferably, the improved contamination monitor should be capable of being programmed to take information from the liquid system at preselected periods of time and should be capable of providing recognizable output information so as to indicate to the operator the specific nature of any abnormal condition such as an excessively fast rate of filter plugging.

The present invention is directed to overcoming one or more of the problems as set forth above.

DISCLOSURE OF THE INVENTION

In accordance with one aspect of the present invention a contamination monitor for sensing particle contamination in a liquid system having a filter includes sensor means for producing a signal related to the pressure differential across the filter, reference means for producing a reference signal related to at least one of the viscosity changes and flow changes of the liquid, and processing means for receiving the signals from the sensor means and the reference means and providing a recognizable compensated output corresponding to the contamination level of the liquid system.

In accordance with a further aspect of the invention a method of monitoring the contamination level of a liquid system having a filter includes the steps of producing a signal related to the pressure drop across the filter and directing it to a data processor and interface unit, providing reference means capable of delivering one or more reference signals to the data processor and interface unit to compensate for variations in at least one of the viscosity of the liquid and the flow passing through the filter, and manipulating the signal information in the data processor and interface unit and directing a plurality of command signals to an operator display unit indicating certain normal and abnormal operating conditions thereof.

More specifically, a preferred embodiment of the contamination monitor includes a first differential pressure transducer across the service filter, a second differential pressure transducer across a reference sieve in downstream communication with the filter, and a programmed data processor and interface unit that manipulates the information from the pressure transducers and provides a plurality of command signals useful for informing the operator through a suitable display unit. Advantageously, the reference sieve provides a reference differential pressure that allows a microprocessor within the data processor and interface unit to correct for variations in flow and/or temperature and to calculate relatively accurate values for the filter load and the plugging rate. Another major role for the contamination monitor is as a diagnostic tool to help define whether the observed conditions are normal or abnormal. For example, if the rate of filter plugging is beyond preselected limits a signal could be delivered to the operator alerting him of the potential problem. Recognition of the probable cause of an abnormal condition can suggest action to be taken to correct it by the operator of the system or by maintenance personnel.

BEST MODE FOR CARRYING OUT THE INVENTION

Figure 1:
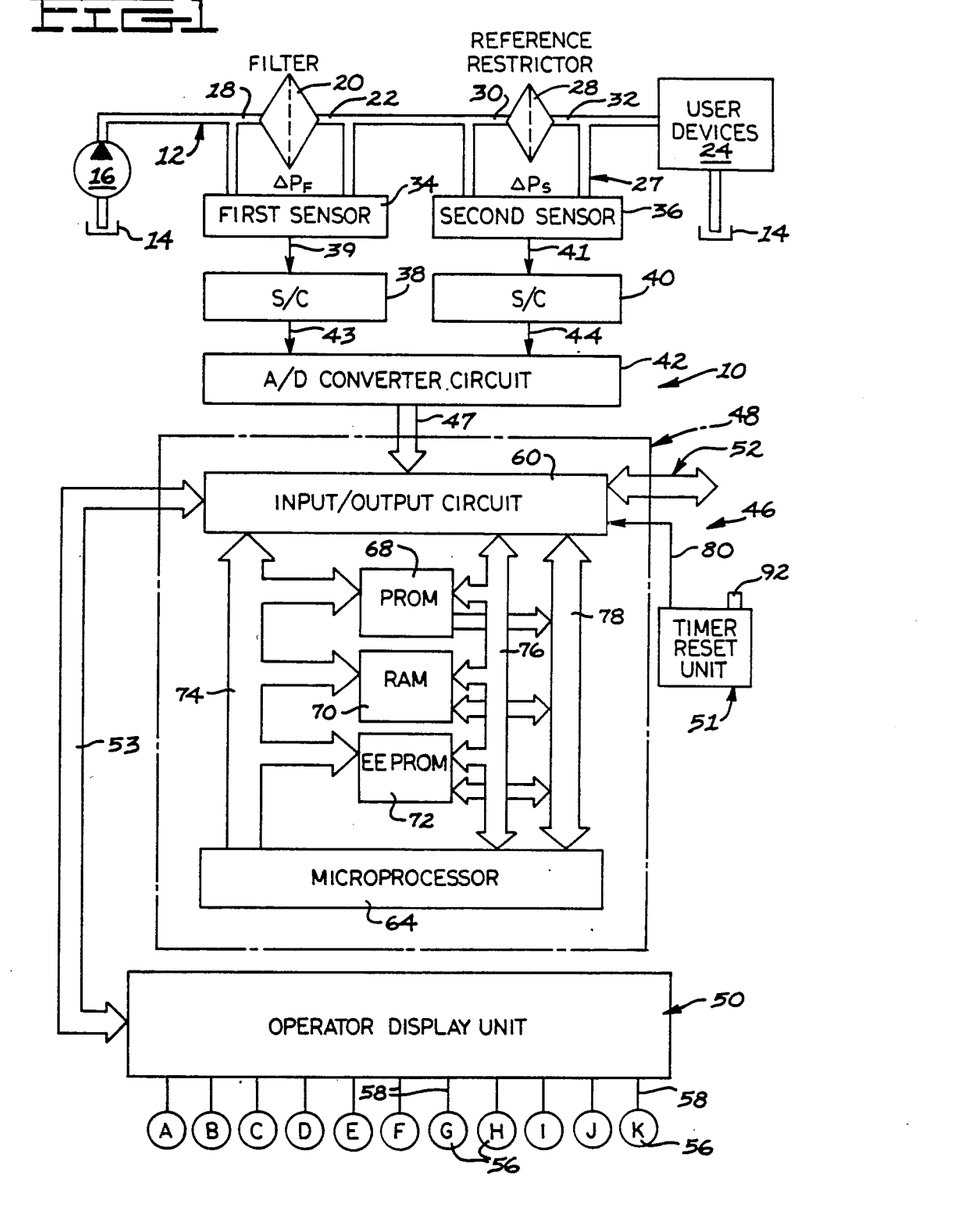
FIG. 1 is a block diagram of the contamination monitor of the present invention in conjunction with an exemplary liquid system having a service filter.

Referring to FIG. 1, there is shown a contamination monitor 10 constructed in accordance with the present invention for a liquid system 12 such as can be used in the hydraulic system of a vehicle. The liquid system includes a reservoir 14, a pump 16 adapted to direct fluid under pressure from the reservoir to an inlet passage or first inlet 18 leading to a conventional filter 20. The filter desirably removes foreign debris or deleterious material, whether metallic or non-metallic, from circulation in the liquid of a size larger than a minimum diameter, determined by the filter design, for example larger than 10 micrometers. The filtered liquid exits from an outlet passage or first outlet 22 and is normally directed to one or more user devices 24 of any conventional type. A relief valve, not illustrated, is typically connected to the liquid system to limit the maximum pressure therein to a preselected value commensurate with the services the user devices are adapted to perform.

The contamination monitor 10 includes a reference apparatus 27 having a reference restrictor or sieve 28 defining a second inlet 30 in downstream communication with the first outlet 22 from the service filter 20, and a second outlet 32 in upstream communication with the user devices 24. Advantageously, the sieve is employed for providing a pressure drop that can be compared with the pressure drop across the service filter. A sieve such as a meshed screen having relatively coarse pores, for example having a size of about 100 micrometers, can produce a pressure drop approximately equal to or at least comparable to the pressure drop across the clean filter 20. As the viscosity and the flow of the liquid vary the respective pressure drops across the filter and sieve would advantageously increase or decrease together in a tracking relationship, and the ratio of the pressure drops is advantageously substantially independent of viscosity and flow.

The contamination monitor 10 further includes a first sensor or differential pressure transducer 34 connected between the first inlet 18 and first outlet 22 for continuously measuring the pressure differential across the service filter 20, and the reference apparatus 27 includes a second sensor or differential pressure transducer 36 connected between the second inlet 30 and second outlet 32 for continuously measuring the pressure differential across the reference sieve 28. The first differential pressure transducer 34 is conventional and directs a first electric signal to a first signal conditioner 38 via a line 39. In a like manner the second differential pressure transducer 36 is conventional and directs a second electric signal to a second signal conditioner 40 via a line 41. These transducers can be non-linear since a normal filter contamination curve is non-linear. A converter circuit 42, such as an analog-to-digital (A/D) converter circuit, receives the signals from the conditioners on lines 43 and 44 respectively, converts them from analog to digital form, and delivers them to a processing means 46 by a communications link 47.

Basically, the processing means 46 includes a data processing and interface unit 48, an operator display unit 50, a timer reset unit 51, and an external interface connection 52. The data processing and interface unit 48 receives the processed sensor signals from the communications link 47 and provides the diagnostic routine which generates and directs command signals to the operator display unit 50 via a line or cable 53. In the instant embodiment the operator display unit 50 internally includes a light-emitting diode driver, not shown, for lighting at least one of a plurality of light-emitting diodes or lights 56 in the vicinity of the operator. As will be later described the lights, individually identified by the letters A through K, are each associated with a specific operating mode of the liquid system 12 to enable the operator to immediately monitor the condition of the liquid system. The lights are each connected to the internal LED driver by separate connecting lines 58.

While the instant embodiment employs an array of light-emitting diodes 56, other embodiments employing a liquid crystal display or a vacuum fluorescent display could be used for visual communication with the operator. An audio signal may also be employed when an abnormal and potentially harmful condition occurs.

The data processor and interface unit 48 includes an input/output circuit 60 connected to the input communications link 47. Preferably, the input/output circuit includes such conventional componentry as an internal clock or programmable timer module, a peripheral interface adapter, and an asynchronous control interface adapter, although not shown in FIG. 1. The data processor and interface unit also includes a microprocessor or CPU unit 64, a programmable read-only memory circuit (PROM) 68, a random access memory or volatile memory circuit (RAM) 70, and an electrically erasable programmable read-only memory circuit (EEPROM) or nonvolatile memory circuit 72. An address bus 74, a control bus 76 and a data bus 78 are used to transmit information between the microprocessor and the various circuits in a well known manner as is diagrammatically illustrated. In general, the PROM circuit 68 functions to permanently store the diagnostic program steps of the contamination monitor 10 and the predetermined technical information relative to the characteristics of a specific type of service filter 20. The RAM circuit 70 functions to actively process and temporarily store information from the microprocessor 64 and PROM circuit 68, but can lose such information when the electrical power is shut off. And the EEPROM circuit 72 functions to retain certain diagnostic information indefinitely for later recall despite the shut off of electric power to the data processor and interface unit 48.

The microprocessor 64 processes the information received from the input/output circuit 60, as well as the information received from the busses 74, 76 and 78 and directs the appropriate command signals to the operator display unit 50 via the cable 53. The external interface connection 52 associated with the input/output circuit serves merely as another communications link to an operator or maintenance person interested in more detailed historical information or more precise numerical data on the operation of the liquid system 12 from the time the clean filter 20 was installed to the time of the check-out than would be provided by the visual readout information of the lights A-K.

The timer reset unit 51 is connected to the input/output circuit 60 by a line 80, and includes a reset button or switch 92 effective when depressed to tell the input-/output circuit when a new filter 20 has been installed, or in other words to reset the internal clock of the input-/output circuit and to prepare the data processor and interface unit 48 for taking new data.

INDUSTRIAL APPLICABILITY

Figure 3:
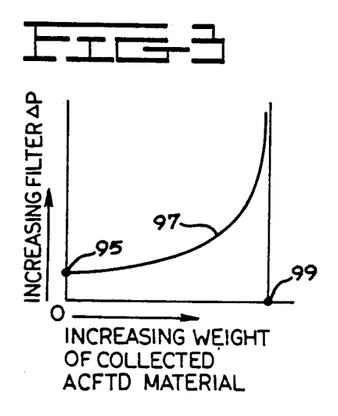
FIG. 3 is a graph showing pressure drop plotted against various weight amounts of collected standard dust material (ACFTD) of a preselected filter.

As is known in the art, the pressure drop across a conventional annular folded element type service filter 20 increases as the filter loads up with contaminant materials and this relationship can be appreciated by reference to FIG. 3. The initial clean filter pressure drop is indicated by the point 95, and by adding uniform amounts of a standard fine test dust material to the liquid system at preset intervals of time an operational plugging curve 97 can be obtained. For example, standard ACFTD (dust) material such as is provided by the A.C. Spark Plug Division of General Motors Corporation can be selectively added while maintaining a preselected temperature for viscosity control and while maintaining a preselected flow through the filter. The point 99 is equivalent to the mass of particles collected by the filter which substantially completely plugs all the pores of the filter, or can be referred to as the intrinsic filter capacity M. Since the functional relationship between loading and pressure drop can thus be predicted, it is possible to determine the amount of the filter's accumulated load by measuring the pressure drop across the filter. Moreover, the rate of increase in the pressure drop is related to the rate of increase in the loading which is dependent on the contaminant level in the liquid system 12. One or more formulas can be developed on a preselected filter or group of filters and this information can be preprogrammed into the data processor and interface unit 48. Thereafter, readings taken at preselected intervals of time of the signals from the sensors 34 and 36 can be mathematically manipulated within the contamination monitor to determine the health of the hydraulic system such as by enabling the prediction of the remaining life of the filter 20 if the indicated contamination rate were to persist, and by enabling a good estimate of the actual contamination level that is loading the filter.

The sieve 28 is introduced into the liquid system 12 in order to provide a positive reference having substantially the same functional dependence on viscosity and flow as the filter 20. This provides a separate pressure drop that can be compared with the filter's pressure drop.

Because the pores of the reference sieve 28 are chosen to be larger than the equivalent pores of the filter 20, the sieve should not load up with contaminants. The contamination monitor 10 can continually calculate the ratio of the pressure differential across the sieve and the pressure differential across the service filter, and it is to be appreciated that such ratio is substantially independent of viscosity and flow and is proportional to the filter's reserve capacity. If the loading rate is constant, as is indicated by the inclined broken line 101 in FIG. 4, the filter's life L can be projected to its intrinsic filter capacity M.

Figure 4:
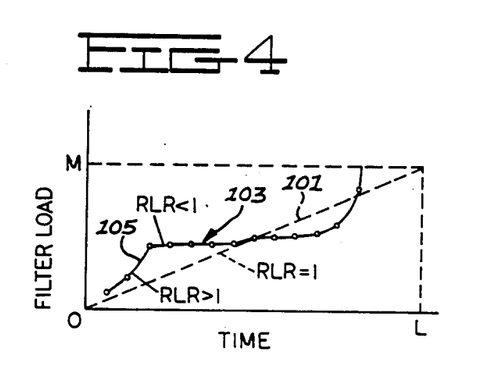
FIG. 4 is a graph illustrating the theoretical history of a filter by plotting its filter load against time and which data can be provided by the contamination monitor of FIG. 1.

As can be noted by reference to FIG. 4, the broken line 101 represents a relative loading rate (RLR) of "1". The relative loading rate (RLR) is equal to the actual instantaneous filter loading rate divided by the constant filter loading rate that would just plug a typical one of the filters 20 in its design life L. A conceivable filter load history could be recorded within the memory of the contamination monitor 10 as is represented by the solid line 103 in FIG. 4 that connects the plurality of individual filter load readings taken by the contamination monitor and stored in the EEPROM 72. A relative loading rate appreciably greater than 1 is apparent at region 105 on the line 103, and this could be cause for concern to an operator as it represents an abnormally fast rate of accumulated particles in the service filter. For example, a seal, bearing or other element in the user device 24 may be experiencing failure such as to contaminate the liquid system with debris.

Figure 2:
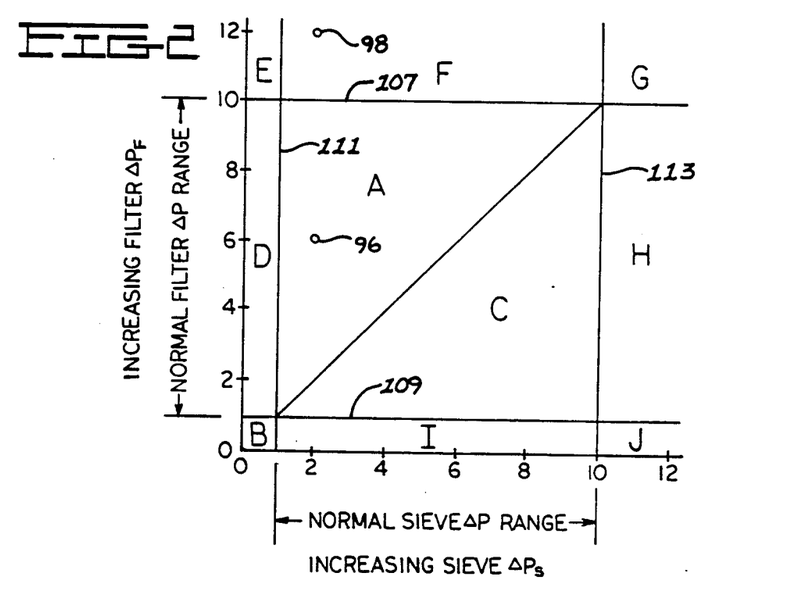
FIG. 2 is a diagnostic logic graph plotting the pressure drop across the service filter of FIG. 1 versus the pressure drop across a reference restrictor of the contamination monitor of FIG. 1 which is useful for understanding the various operating modes of the contamination monitor.

Referring to the diagnostic graph illustrated in FIG. 2, the pressure drop across the filter 20 is plotted vertically versus the pressure drop across the sieve 28. This theoretical graph is plotted without precisely identified unit pressures so as to be generally applicable to a wide range of filters. Normal operation for the representative filter and representative sieve are taken to be between 1 and 10 units by way of example. Under normal conditions the filter cannot have a pressure drop less than that of the sieve. This at least partly defines a triangular region for normal operation of the service filter which is designated zone A in FIG. 2. Any point lying outside triangular zone A would signify an abnormal condition. For example, suppose the data processor and interface unit 48 receives signals from communications link 47 corresponding to unit differential pressures $\Delta P_F = 6$ and $\Delta P_S = 2$. This reference point, designated 96 on the graph, lies within the normal triangular zone A so as to permit the microprocessor 64 to proceed with calculation of the filter load and loading rate for that instant of time. However, if the signals from link 47 are equivalent to unit differential pressures $\Delta P_F = 12$ and $\Delta P_S = 2$, as shown by reference point 98, the point that is plotted would lie outside zone A and would reside in the zone identified by the letter F where the microprocessor could not calculate a meaningful filter load. In the second instance something would be abnormal.

The data processor and interface unit 48 can be programmed to alert the operator whenever there exists such abnormal conditions. The operational zones or regions between the lines as identified by the letters A-J in FIG. 2 can be defined, for example, by the unit limits on the graph and this information can be preprogrammed into the data processor and interface unit. Accordingly, any intersecting point plot of the respective differential pressures in the zones of the graph can be equated to a probable cause of the abnormal condition as follows:

| Zone | Probable cause |
|---|---|
| A | Normal - no problem |
| B | Abnormal - low flow |
| C | Abnormal - damaged filter |
| D | Abnormal - damaged sieve |
| E | Abnormal - plugged filter |
| F | Abnormal - plugged filter |
| G | Abnormal - cold oil |
| H | Abnormal - plugged sieve |
| I | Abnormal - damaged filter |
| J | Abnormal - plugged sieve; damaged filter |

Figure 5:
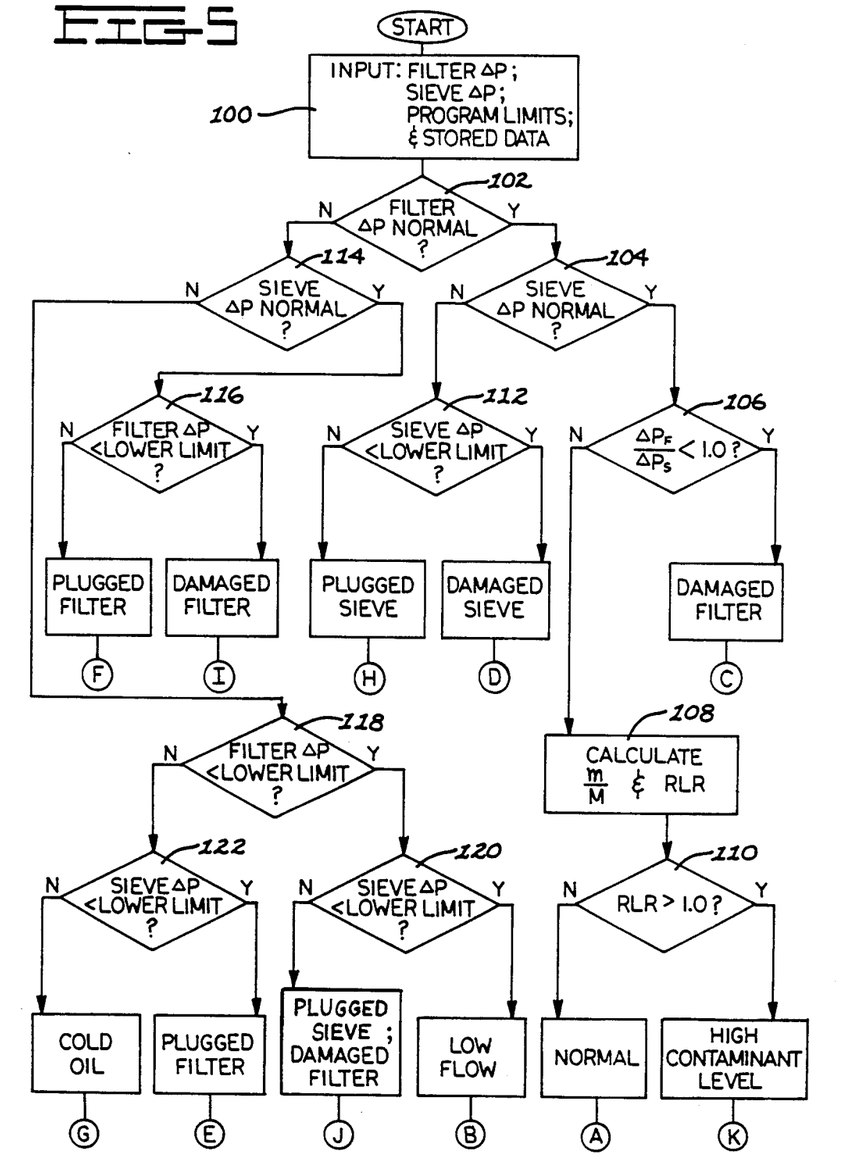
FIG. 5 is a diagnostic logic flow chart for the contamination monitor of FIG. 1 which is helpful in understanding when a light in the operator display unit of the contamination monitor is able to indicate a particular operating mode.

The diagnostic logic flow chart illustrated in FIG. 5 is illustrative of one exemplary control system that can be employed within the data processor and interface unit 48. Initially, the memory of the unit 48 can be supplied with the following data:

Filter: lower and upper pressure drop limit values, the capacity M, the expected filter life L, and the filter plugging rate alarm value Sieve: lower and upper pressure drop limit values Assuming a new filter 20 is installed in the liquid system 12 of FIG. 1, the reset button 92 can be depressed by the vehicle operator to establish the starting of a new time frame by the clock in the input/output circuit 60. At that time the data processor and interface unit 48 reads the pressure drop across the filter and across sieve 28 as is diagrammatically shown by a block 100 in FIG. 5. Block 100 and the blocks that follow are to be understood as being integrated portions of the data processor and interface unit 48. A decision block 102 then determines whether the filter pressure condition is normal such as would be the case if the pressure drop is on or within preestablished horizontal lines 107 and 109 in FIG. 2. If it is normal, another decision block 104 determines whether the sieve pressure condition is normal such as would be the case if the pressure drop is on or within preestablished vertical lines 111 and 113 in FIG. 2. If the sieve pressure drop is normal a decision block 106 determines whether the pressure ratio between $\Delta P_F$ and $\Delta P_S$ is less than 1.0 and/or is generally less than a preselected normal range. If it is the system is operating in triangular zone C of FIG. 2, and the data processor and interface unit 48 directs a command signal to the operator display unit 50 sufficient to light the LED 56 identified by the Letter C in FIGS. 1 and 5 and to indicate an abnormally low filter pressure drop probably caused by a damaged filter. An audible alarm signal could alternatively be provided. If the pressure ratio is more than 1 a calculation block 108 is effective to calculate the load ratio of m/M and the relative load rate (RLR), where m is equal to the mass of particles collected in the filter 20 at the time t of measurement. A RLR greater than 1.0, or some other suitable threshold number larger than 1.0 for example, can correspond to a filter plugging rate above the normally expected rate by a preselected degree and represents a high contamination level in the liquid. In such instance a decision block 110 is effective to direct a command signal to the operator display unit 50 sufficient to light the LED identified by the letter K in FIGS. 1 and 5 to indicate this excessively fast rate of filter plugging. An audible alarm signal could alternatively be provided. A RLR value less than 1.0 would result in the LED identified by the letter A being lit and this would indicate the normal operating condition that would prevail the large majority of the time.

Referring to decision block 104 of the diagnostic flow chart in FIG. 5, if the pressure drop across the sieve 28 is not normal another decision block 112 is effective to check whether the pressure drop is below a lower limit value. If it is below the lower limit value the light D is lit indicating a damaged sieve, and if it is not the light H is lit indicating a plugged sieve.

Referring back to decision block 102, if the filter pressure drop is abnormal a decision block 114 checks whether the reference sieve pressure drop is normal. If it is a decision block 116 checks whether the filter pressure drop is below a lower preestablished limit. If it is below the lower limit value the microprocessor 64 causes the light I to be lit via input/output circuit 60, cable 53, and operator display unit 50 indicating a damaged filter. If it isn't, the light F is lit indicating the probable cause of the abnormal condition is a plugged filter.

On the other hand, if the decision block 102 indicates an abnormal filter pressure drop and the reference block 114 indicates that the sieve pressure drop is abnormal another diagnostic flow path is activated to a decision block 118. If the filter pressure drop is below the lower limit value a decision block 120 is useful for determining whether the sieve pressure drop is below its lower limit value and, if it is, the light B is lit indicating a low flow condition. If the sieve pressure drop is not below the lower limit value it is above the upper limit value and the block 120 serves to light light J indicating a plugged sieve or a damaged filter.

Lastly, if the decision block 118 indicates the filter pressure drop is not below its lower limit value then a decision block 122 serves to light light G if the sieve pressure drop is not below its lower limit value, and to light light E if the sieve pressure drop is below its lower limit value to indicate to the vehicle operator either cold oil or a plugged filter respectively.

The informational history regarding operation of the individual lights 56 may be retained in the EEPROM circuit 72 for later analysis.

Alternate Embodiment

Figure 6:
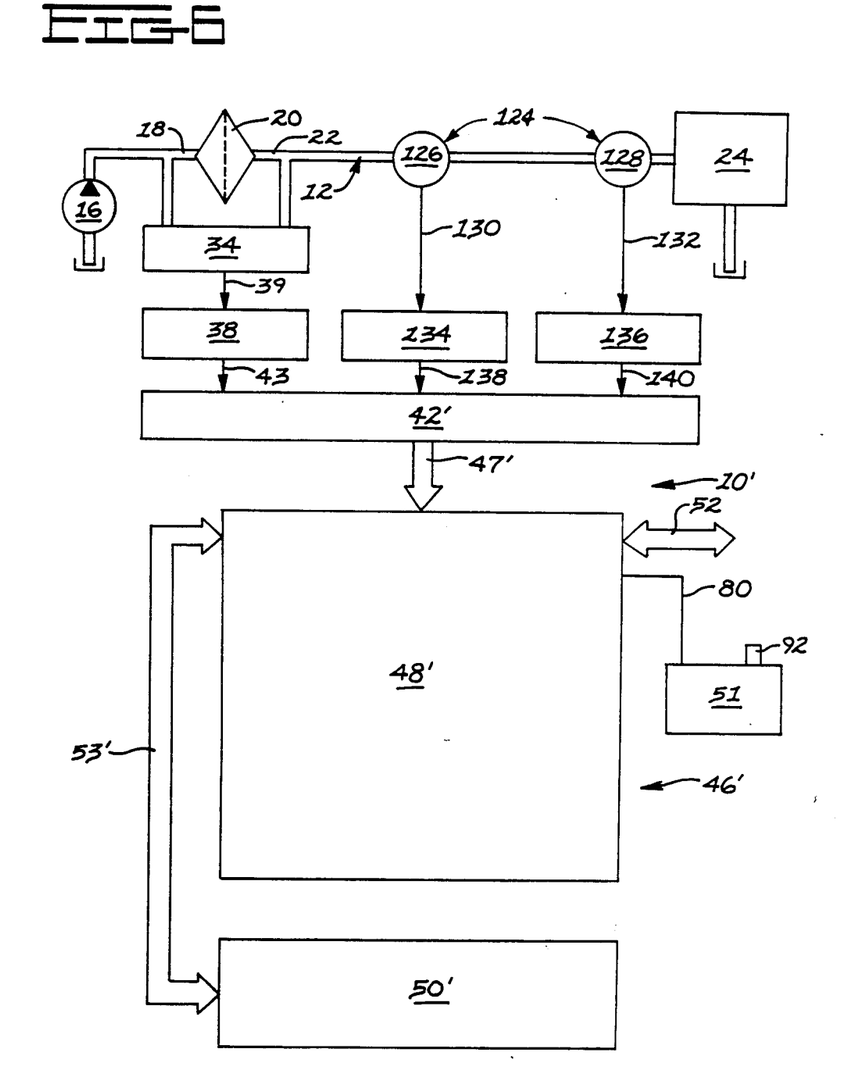
FIG. 6 is a block diagram of an alternate embodiment contamination monitor constructed in accordance with the present invention that may be compared with the preferred embodiment of FIG. 1.

FIG. 6 shows an alternate embodiment contamination monitor 10' that incorporates a similar first sensor or pressure transducer 34 across the filter 20 as in the preferred embodiment. But rather than employing the reference restrictor 28 and the second sensor 36 used in the reference apparatus 27 of the preferred embodiment, a somewhat more complex reference apparatus 124 is provided for accommodating changes in flow through the filter and changes in the viscosity of the liquid due to temperature variations. Particularly, reference apparatus 124 includes a flow sensor or flow meter 126 for measuring flow of liquid through the filter and a conventional analog temperature sensor or temperature transducer 128 for measuring the liquid temperature, each of which is effective to direct electrical analog signals proportional thereto via a line 130 or a line 132 to second and third signal conditioners 134 and 136 respectively. A modified A/D converter circuit 42' is in communication with the signals from the three signal conditioners through the first line 43, a second line 138, and a third line 140 respectively. It is contemplated that a modified data processor and interface unit 48' would receive the information from the communications link 47' and would be preprogrammed with the upper and lower pressure drop limit values of the specified filter, and generally the plugging characteristics of the filter, for a range of liquid flow and for a range of temperatures, as well as for the fully loaded contamination level M thereof. A modified program would be used to input information into the microprocessor within the unit 48'. And, the display unit 50' could be modified so that the LED lights thereof, not shown, could indicate diagnostic information relative to whether the flow meter and temperature transducer were operating in normal or abnormal regions.

It is contemplated that a conventional pressure by-pass valve, not shown, can be connected across both the filter 20 and reference sieve 28 of FIG. 1 to enable high pressure liquid in the inlet passage 18 to be communicated directly to the second outlet 32 upon reaching a preselected pressure. Such a by-pass valve would substantially not affect the operation of the contamination monitor 10.

In view of the above, it can be appreciated that the contamination monitors 10 and 10' of the present invention are both based on continuously measuring the pressure drop across the primary service filter 20, on providing reference signal means 27 or 124 for compensating for variations in viscosity and flow, and on directing this information to a programmed data processor and interface unit 48 for performing desirable mathematical interrogation, storing of information, calculations and providing the appropriate command signals to an operator display unit 50. Particularly, the contamination monitors can desirably compare a change in the actual rate of plugging of the filter from a known normal rate of filter plugging to alert the operator of a potential problem. In fact, the instant contamination monitors can be programmed to test each data set immediately for abnormal changes in value and, if some irregularity was noted, can be programmed for additional tests and data output. Such early and accurate indications can reduce the total service costs, can reduce the cost for down time and repairs from contaminant induced failures, can increase the life of associated equipment, and can be used to stop the vehicle, engine or the like when an excessively fast rate of filter plugging is observed and prior to major system damage.

At a minimum the contamination monitor 10 should tell the operator when the contamination level is abnormally high and when the filter 20 is nearly plugged. But as described above much valuable and detailed information can be supplied to the operator by the plurality of lights A-K or comparable display. Finding the best display path or warning system to follow requires "Ergonomics", the study of operator response to information in the work environment.

It should be recognized that while the contamination monitors 10 and 10' compensate for both viscosity and flow variations of the liquid passing through the filter 20, the contamination monitors are also useful for compensating for changes in one of these parameters when the remaining parameter is relatively constant. In a constant flow system, for example, it would only be necessary for the data processor and interface unit 48' to receive the signal from the differential pressure transducer 34 and to receive a compensating signal from the temperature transducer 128 in order to obtain a reliable indication of the contamination level of the liquid system through the internal program of the contamination monitor. On the other hand, in indoor systems where the temperature is a relatively constant value, only flow needs to be compensated for by the contamination monitor.

Other aspects, objects and advantages will become apparent from a study of the specification, drawings and appended claims.

What is claimed is:

1. A contamination monitor for continuously sensing particle contamination in a liquid system having a filter, comprising:
    sensor means for producing a first electrical signal related to the pressure differential across the filter;
    a reference restrictor in downstream communication with the filter;
    reference sensor means for producing a second electrical signal related to the pressure differential across the restrictor; and
    processing means including a programmable data processor and memory unit for receiving the first and second electrical signals and providing a recognizable compensated output corresponding to the contamination level of the liquid system.

2. The contamination monitor of claim 1 wherein the processing means includes a display unit connected to the programmable data processor and memory unit and having a plurality of indicators for providing visual information to an operator indicative of the diagnostic health of the liquid system.

3. The contamination monitor of claim 2 wherein the reference restrictor is a sieve, the sensor means includes a first differential pressure transducer connected across the filter, and the reference sensor means includes a second differential pressure transducer connected across the sieve.

4. The contamination monitor of claim 3 wherein the programmable data processor and memory unit includes a microprocessor and the processing means includes means for measuring time starting with the initial installation of the filter.

5. The contamination monitor of claim 1 wherein the reference restrictor is a sieve having pores larger than the equivalent pores of the filter, the data processor and memory unit being of a construction sufficient for periodically calculating the ratio of the pressure differential across the sieve and the pressure differential across the filter.

6. The contamination monitor of claim 1 wherein the programmable data processor and memory unit includes microprocessor and memory means for storing for later retrieval preselected items of information, continually calculating the pressure ratios between the signals and the time rate of change thereof, and generating a plurality of command signals corresponding thereto.

7. The contamination monitor of claim 6 wherein the programmable data processor and memory unit includes means for resetting the microprocessor and memory means when a new filter has been installed and establishing the time interval of use of the filter.

8. A contamination monitor for continuously sensing particle contamination in a liquid system including a filter having a first inlet and a first outlet, comprising:
    a reference sieve of preselected coarseness having a second inlet and a second outlet, the second inlet being in downstream communication with the first outlet;
    first sensor means for producing a first electrical signal relatable to the pressure differential between the first inlet and the first outlet;
    second sensor means for producing a second electrical signal relatable to the pressure differential between the second inlet and the second outlet; and
    data processor and interface unit means responsive to the first and second electrical signals for providing a recognizable output corresponding to the contamination level or diagnostic health of the liquid system, the data processor and interface unit means including a microprocessor, memory circuit means for storing information, and means for measuring time.

9. The contamination monitor of claim 8 wherein the first sensor means and the second sensor means individually include a differential pressure transducer.

10. The contamination monitor of claim 8 wherein the data processor and interface unit means is of a construction sufficient for calculating the pressure ratios between the signals and the time rate of change thereof.

11. The contamination monitor of claim 8 including an operator display unit having a plurality of lights, the data processor and interface unit means being effective to electrically light one of the lights when filter reaches a loaded condition.

12. A contamination monitor for a liquid system having a filter, comprising:
   first means for producing a first electrical signal related to the pressure differential across the filter;
   a sieve of preselected coarseness in downstream communication with the filter;
   second means for producing a second electrical signal related to the pressure differential across the sieve;
   a display unit; and
   a data processing and interface unit of a construction sufficient for receiving the first electrical signal, compensating for variations in viscosity and flow in response to receiving the second electrical signal, and providing a corrected output to the display unit corresponding to the contamination level of the filter.

13. A contamination monitor for detecting an abnormally high level of particulate contamination in a liquid system having a filter, comprising:
   sensor means for producing an electrical signal representative of the pressure differential across the filter, said pressure differential increasing with time at a known rate for a normal level of contamination of the liquid;
   reference means in downstream communication with the filter for producing an electrical reference signal indicative of the pressure drop thereacross substantially independent of the level of particulate contamination in the liquid; and
   processing means for receiving the electrical signals from the sensor means and the reference means and providing an output signal indicating a change in the pressure differential across the filter which deviates from said known rate by a preselected amount so as to indicate an abnotmally high level of contamination in the liquid system, the processing means including a microprocessor, memory circuit means for storing information, and means for measuring time.

14. A method of monitoring the contamination level of a liquid system having a filter, comprising:
   (a) producing an electrical signal related to the pressure differential across the filter and directing it to a programmable data processor and interface unit;
   (b) providing reference means downstream of the filter for delivering a reference electrical signal to the data processor and interface unit indicative of variations in at least one of the viscosity of the liquid and the flow passing through the filter; and
   (c) manipulating such electrical signal information in the data processor and interface unit and directing a plurality of command signals to an operator display unit indicating certain normal and abnormal operating conditions of the filter and the liquid system.

15. The method of claim 14 wherein step (b) includes producing a reference electrical signal related to the pressure differential across a reference sieve having a preselected coarseness located downstream of the filter.

16. The method of claim 15 wherein step (c) includes calculating the ratio of the pressure differentials and the time rate of change thereof.

17. The method of claim 14 wherein step (c) includes automatically taking readings of the signals at preselected intervals of time, and storing such information for later retrieval.

* * * * *